(12) United States Patent
Nagai et al.

(10) Patent No.: US 8,557,598 B2
(45) Date of Patent: Oct. 15, 2013

(54) METHOD FOR MEASURING BLOOD SAMPLE AND APPARATUS THEREOF

(75) Inventors: Takaaki Nagai, Kobe (JP); Masaharu Shibata, Kobe (JP)

(73) Assignee: Sysmex Corporation, Kobe (JP)

( * ) Notice: Subject to any disclaimer, the term of this patent is extended or adjusted under 35 U.S.C. 154(b) by 1513 days.

(21) Appl. No.: 11/378,402

(22) Filed: Mar. 17, 2006

(65) Prior Publication Data

US 2006/0228807 A1  Oct. 12, 2006

(30) Foreign Application Priority Data

Mar. 17, 2005 (JP) ................. 2005-077138

(51) Int. Cl.
*G01N 33/48* (2006.01)
*G01N 35/02* (2006.01)

(52) U.S. Cl.
USPC ............... 436/164; 422/65; 422/82; 422/50; 422/66; 422/67

(58) Field of Classification Search
USPC ......... 436/164; 422/65, 67, 50, 66; 73/864.82
See application file for complete search history.

(56) References Cited

U.S. PATENT DOCUMENTS 3,549,994 A * 12/1970 Rothermel et al. .......... 324/71.1
4,387,076 A *  6/1983 Cabrera et al. ................ 422/67
4,418,039 A * 11/1983 Adler ............................. 422/82

FOREIGN PATENT DOCUMENTS

JP  S58-076765 A  5/1983
JP  2001-153762 A  6/2001

* cited by examiner

*Primary Examiner* — Krishnan S Menon
*Assistant Examiner* — Rebecca M Fritchman
(74) *Attorney, Agent, or Firm* — Brinks Hofer Gilson & Lione

(57) ABSTRACT

The present invention relates to a method for measuring a blood sample comprising the steps of: communicating the inside of a sealed container with atmosphere by piercing a cap for sealing the sealed container; supplying a diluted solution from the base end side of the aspiration pipe to fill the aspiration pipe with the diluted solution; aspirating the blood sample in the sealed container; discharging the aspirated blood sample into a measurement sample preparing container; and measuring a measurement sample prepared in the measurement sample preparing container.

13 Claims, 15 Drawing Sheets

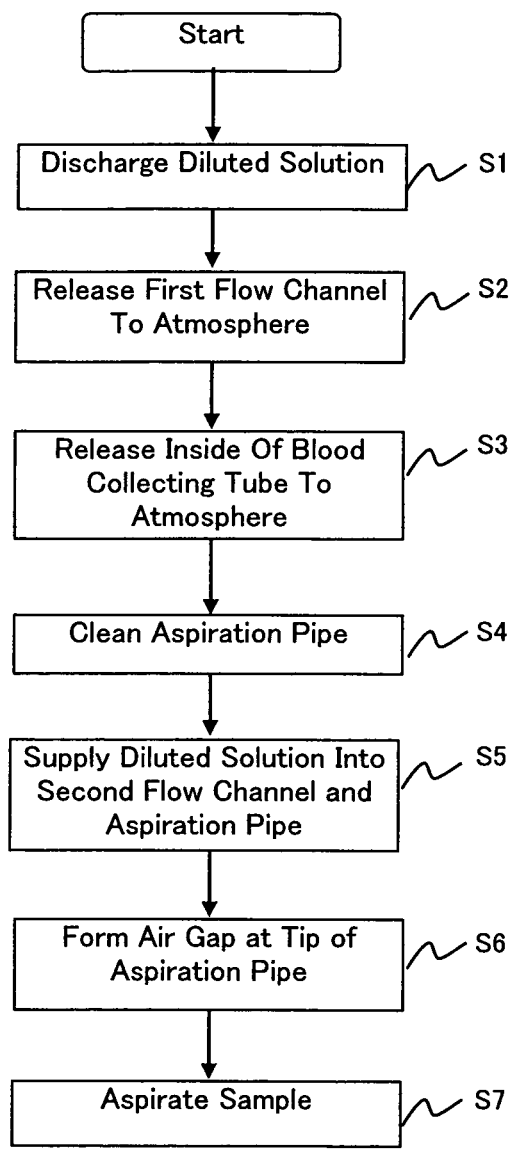

METHOD FOR MEASURING BLOOD SAMPLE AND APPARATUS THEREOF

This application claims priority under 35 U.S.C. §119 to Japanese Patent Application No. 2005-077138 filed Mar. 17, 2005, the entire content of which is hereby incorporated herein by reference.

TECHNICAL FIELD

The present invention relates to a method and apparatus for measuring a blood sample. More particularly, the present invention relates to a method and apparatus for aspirating and measuring a blood sample (hereinafter, also merely referred to as "sample") in a sealed container sealed by a cap.

BACKGROUND

A sample aspiration pipe which has a aspiration thin tube for aspirating a sample and a ventilation thin tube for performing a ventilation in a container at the time of aspiration, and punctures the cap by using both the thin tubes has conventionally been known as the sample aspiration pipe for aspirating a liquid sample in a sample container sealed by a cap such as a rubber cap (for example, see Japanese Patent Application Laid-Open (JP-A) No. 58-76765).

The sample aspiration pipe disclosed in Japanese Patent Application Laid-Open (JP-A) No. 58-76765 is a main constituent element of a sample feed device for aspirating and supplying the sample in a seal pipe to an automatic sample inspection device, and have a coaxial structure where two thin tubes are arranged in the same axis. That is, a ventilation thin tube is provided on the same axis as a aspiration thin tube on the outer circumference of the aspiration thin tube having a center passing hole. The sample in a seal pipe is sucked via the center passing hole. On the other hand, the inside of the seal pipe is ventilated with atmosphere via a flow channel between the aspiration thin tube and the ventilation thin tube at the time of aspirating.

However, since the sample aspiration pipe has a structure where two thin tubes are arranged on the same axis, the manufacture is difficult, and thereby the cost is high. Since it is necessary to clean the outer circumferences of two thin tubes, there is a problem in that a cleaning step is complicated.

On the other hand, a sample aspiration/discharging device for piercing a cap by using a aspiration needle to releasing the inside of a container to atmosphere, extracting the aspiration needle from the cap, cleaning the outside and inside of the aspiration needle, and piercing the cap by using the aspiration needle again to suck the liquid sample has been known as a sample aspiration/discharging device for aspirating and discharging the liquid sample in the sample container sealed by the cap using the aspiration needle (for example, see Japanese Patent Application Laid-Open (JP-A) No. 2001-153762).

However, when aspirating small amount of liquid sample while determining the quantity of the liquid sample, there is a problem in that the quantification accuracy for determining the quantity is insufficient in the device described in Japanese Patent Application Laid-Open (JP-A) No. 2001-153762.

The sample aspiration/discharging device holds the sealed container so that the cap is located below, and punctures the cap using the aspiration needle toward the top from the bottom to release to atmosphere. After the sample aspiration/discharging device extracts the aspiration needle from the cap, the sample aspiration/discharging device reverses a aspiration needle, soaks the tip in a cleaning tub to clean the inside of the aspiration needle, and the sample aspiration/discharging device punctures the cap using the aspiration needle again to suck the liquid sample. Thereby, the cleaning device for cleaning the outside of the aspiration pipe and the cleaning tub for cleaning the inside of the aspiration pipe are required, and the device constitution and a sequence for aspirating the liquid sample are complicated.

SUMMARY

An object of the present invention provides a method and apparatus for measuring a blood sample capable of enhancing quantification accuracy when aspirating the blood sample using a aspiration pipe.

Another object of the present invention provides a method and apparatus for measuring a liquid sample capable of aspirating and measuring the blood sample by simple constitution or sequence.

The first aspect of the present invention relates to a method for measuring a blood sample, comprising the steps of: piercing a cap for sealing a container by using an aspiration pipe and inserting the tip of the aspiration pipe into the sealed container to communicate the inside of the sealed container with atmosphere; drawing out the aspiration pipe from the sealed container and supplying a diluted solution from the base end side of the aspiration pipe to fill the aspiration pipe with the diluted solution; piercing the cap using the aspiration pipe and inserting the aspiration pipe into the sealed container to aspirate the blood sample in the sealed container; discharging the aspirated blood sample into a measurement sample preparing container; and measuring a measurement sample prepared in the measurement sample preparing container.

The second aspect of the present invention relates to an apparatus for measuring a blood sample, comprising: an aspiration pipe for piercing a cap for sealing a container and aspirating a blood sample in the sealed container; a aspiration pipe moving mechanism for moving aspiration pipe to any position of an outside position of the sealed container, a first position where the inside of the sealed container is released to atmospheric air, and a second position where the blood sample in the sealed container is aspirated; a fluid mechanism having a first flow channel released to atmospheric air, a diluted solution accommodating part for accommodating a diluted solution, a second flow channel capable of connecting the aspiration pipe to the diluted solution accommodating part, a first pump capable of supplying the diluted solution accommodated in the diluted solution accommodating part to the aspiration pipe via the second flow channel, and a second pump capable of aspirating and discharging the blood sample in the sealed container via the second flow channel, and capable of selectively communicating the first and the second flow channels with the aspiration pipe; a measurement sample preparing container for mixing the blood sample with a reagent to prepare a measurement sample; a measuring part for measuring an analysis sample prepared in the measurement sample preparing container; and a controller for controlling the aspiration pipe moving mechanism and the fluid mechanism so that the aspiration pipe is moved to the first position from the outside position, the inside of the sealed container is released to atmospheric air via the first flow channel, the aspiration pipe is moved to the outside position from the first position to supply the diluted solution into the aspiration pipe via the second flow channel.

The third aspect of the present invention relates to a method for aspirating a blood sample, comprising the steps of: piercing a cap sealing a container by using a aspiration pipe and inserting the tip of the aspiration pipe into the sealed container to communicate the inside of the sealed container with atmosphere; drawing out the aspiration pipe from the sealed container and supplying a diluted solution from the base end side of the aspiration pipe to fill the aspiration pipe with the diluted solution; aspirating from the base end side of the aspiration pipe to form an air gap in the tip side of the aspiration pipe; and piercing the cap using the aspiration pipe and inserting the aspiration pipe into the sealed container to aspirate the blood sample in the sealed container.

BRIEF DESCRIPTION OF THE DRAWINGS

FIG. 15 is a flow chart of a method for aspirating a liquid sample according to an embodiment of the present invention.

DESCRIPTION OF THE PREFERRED EMBODIMENTS

Hereinafter, a method and apparatus for aspirating a liquid sample according to the embodiment of the present invention will be explained in detail referring to the accompanying drawings.

Figure 1:
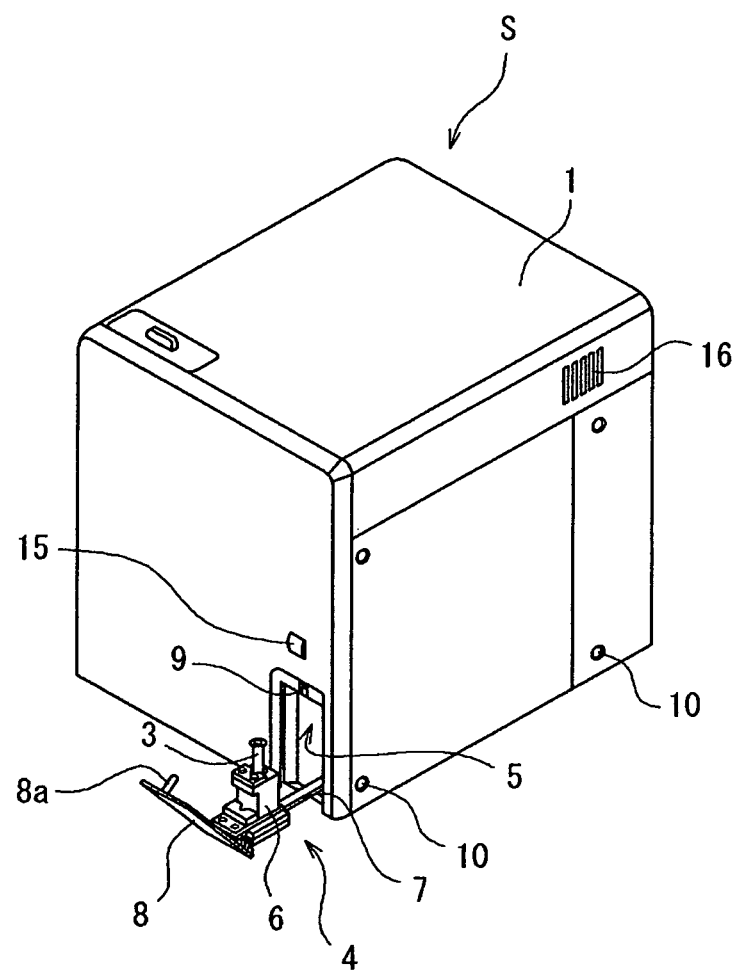
FIG. 1 is an overall perspective view of a sample analysis apparatus containing a liquid sample aspiration device according to an embodiment of the present invention.
Figure 2:
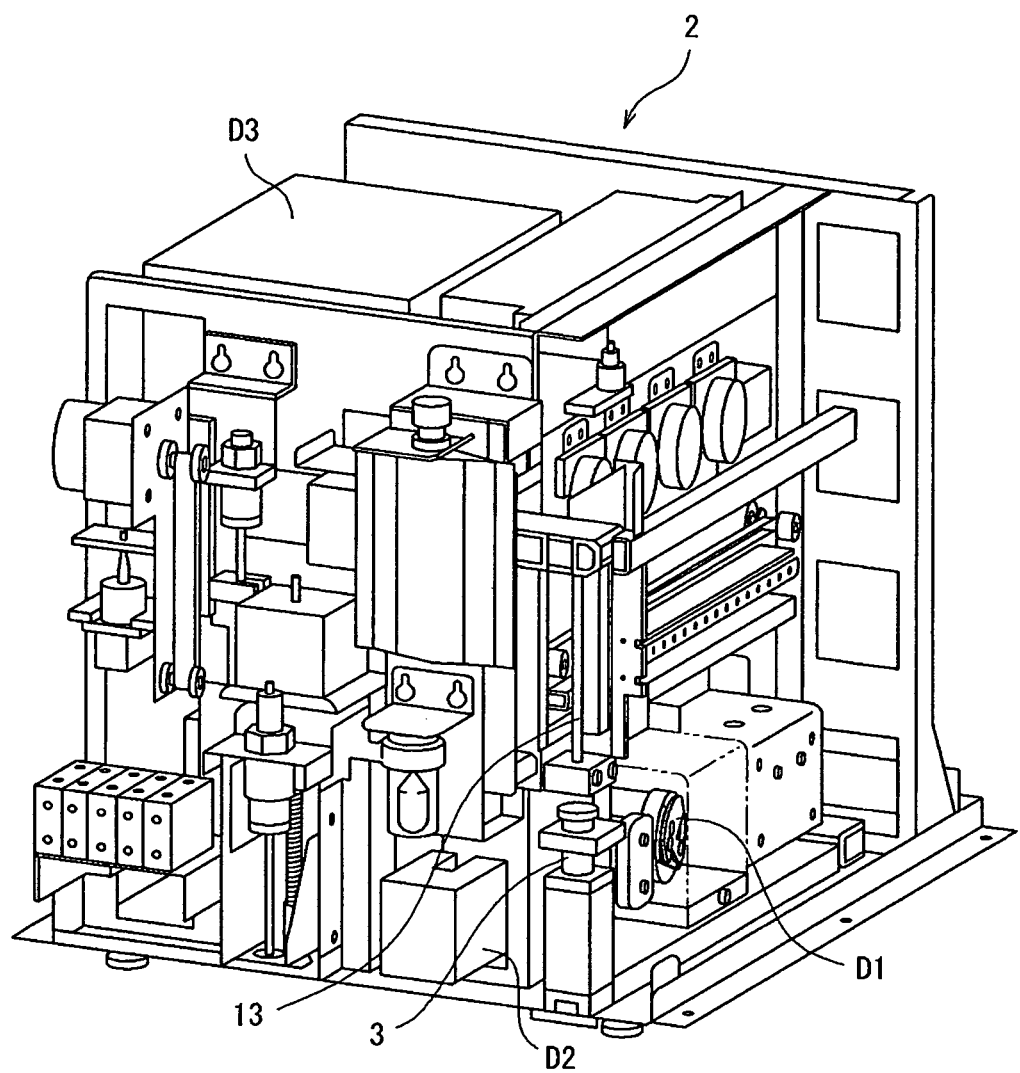
FIG. 2 is a perspective view showing a state where a casing of the sample analysis apparatus shown in FIG. 1 is removed.
Figure 3:
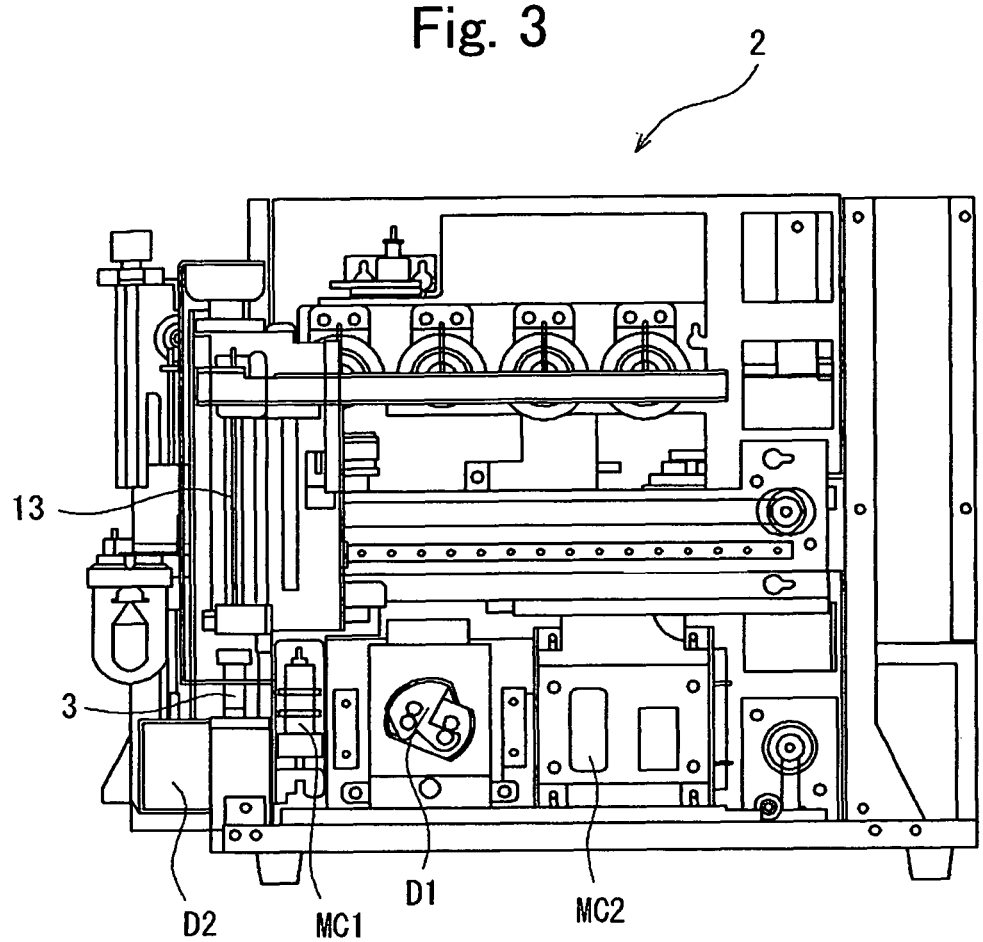
FIG. 3 is a front illustration showing a state where the casing of the sample analysis apparatus shown in FIG. 1 is removed.

FIG. 1 is an overall perspective view of a sample analysis apparatus S containing a liquid sample aspiration device according to an embodiment of the present invention. FIG. 2 is a perspective view showing a state where a casing 1 of the sample analysis apparatus S is removed. FIG. 3 is a front illustration showing a state where the casing is removed.

Figure 14:
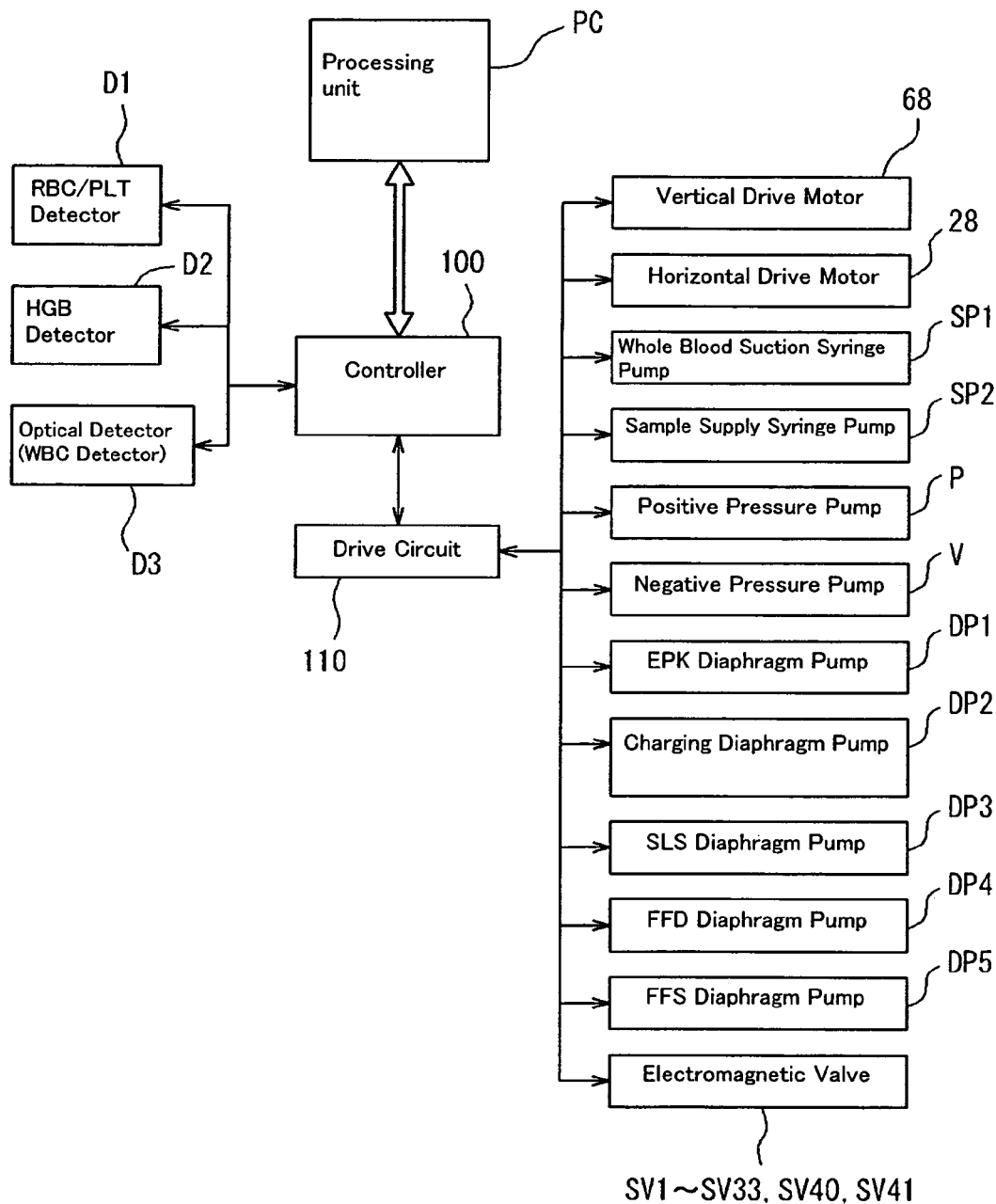
FIG. 14 is a control block diagram of the sample analysis apparatus shown in FIG. 1.

The sample analysis apparatus S is communicably connected to a processing unit PC (typically, a personal computer in which the required computer program is installed) having a display, an input device, a CPU and a memory or the like (see FIG. 14). A sample analysis system is composed of the sample analysis apparatus S and the processing unit PC. A software for a sample analysis apparatus for operating the sample analysis apparatus S, configuring various settings for analysis and displaying analysis results is installed in the processing unit PC. Commands can be applied to the sample analysis apparatus S and measured data can be accepted from the sample analysis apparatus S by the communication between the processing unit PC and the sample analysis apparatus S.

The sample analysis apparatus S is an apparatus (blood analysis apparatus) for measuring blood (sample) accommodated in a blood collecting tube 3 as a sealed container (initial accommodating container of a sample). The sample analysis apparatus S is mainly composed of a apparatus body 2 and a casing 1 for accommodating the apparatus body 2.

The casing 1 is made of a steel plate or the like on which a synthetic resin is applied and which is treated with rust preventing process, and is fixed to the apparatus body 2 using a fixing means such as a bolt. An opening 5 is formed at a lower right part of one face of the casing 1 (a side surface of a left side in FIG. 1), and the blood collecting tube 3 can be inserted into the apparatus body 2 via the opening 5. That is, a slider 7 is movably provided from the opening 5 at the lower end side of the apparatus body 2, and a placing table 6 for placing the blood collecting tube 3 near the end part of the apparatus body 2 is arranged on the slider 7. A cover 8 for closing the opening 5 is rotatably provided at the tip of the slider 7, and the cover 8 is energized to incline to the outside by a predetermined angle by a spring which is not shown (see FIG. 1). When the apparatus is in a non-operating state (this state can be displayed to the outside by non-lighting a lamp in the button 15 provided on one face of the casing 1) and the button 15 is pushed, the slider 7 advances to the outside of the apparatus body 2. When the device is in a non-operating state in that case, the opening 5 is closed by the cover 8. However, the slider 7 advances to the outside of the apparatus body 2, and thereby the engagement of a projection part 8a of the cover 8 and recessed portion 9 formed around the opening 5 is released to open the cover 8. Since the engagement of the projection part 8a and recessed portion 9 is released, the cover 8 is inclined to the outside by a predetermined angle by the energizing force of the spring.

A recessed part (not shown) into which the lower part of the blood collecting tube 3 can be inserted is formed on the upper surface of the placing table 6. When the lower part of the blood collecting tube 3 is inserted into the recessed part, and the button 15 is pushed, the slider 7 retreats into the apparatus body 2, and the blood collecting tube 3 is set to a predetermined position. The cover 8 is then raised so as to resist the energizing force of the spring, and the opening 5 is closed by the cover 8. Since the projection part 8a is engaged with the recessed portion 9 in that case, the cover 8 is prevented from opening. A detector such as a micro switch detects that the opening 5 is certainly closed by the cover 8, and thereby the later sample aspiration step or the like can be performed.

A part of a side surface (a side surface of a right side in FIG. 1) of the casing 1 is fixed to the apparatus body 2 by the bolt 10 so that the check and the maintenance or the like in the apparatus body 2 can be easily performed. In FIG. 1, numeral 16 designates an exhaust port for discharging heat mainly generated in the apparatus body 2 to the outside by a fan (not shown).

The apparatus body 2 is provided with a sample set part 4 for setting the blood collecting tube 3 to a predetermined position in the device, a sample preparation part for determining the quantity of blood in the blood collecting tube 3 and diluting the blood to prepare a mixed sample for analysis, detectors D1, D2, D3 for measuring (detecting) the diluted blood, and a controller for electrically driving and controlling the sample preparation part and the detector. The liquid sample aspiration device of the present invention is composed of an element or mechanism for aspirating the sample from the sealed container among the sample preparation part and the controller.

The sample set part 4 sets the blood collecting tube 3 in which the sample (blood) is accommodated in a sealed state to a predetermined position in the apparatus body 2. The sample set part 4 is composed of the above placing table 6, slider 7 and drive source (not shown) such as a stepping motor driving the slider 7.

The sample preparation part aspirates the blood of a predetermined amount from the inside of the blood collecting tube 3 and mixes the blood with a reagent in a first mixing chamber MC1 or a second mixing chamber MC2 to prepare various analysis mixed samples. The sample preparation part is provided with a aspiration pipe 13 for piercing the cap 3a sealing the inside of the blood collecting tube 3 to suck the sample in the blood collecting tube 3, a horizontal driving part 20 for horizontally moving the aspiration pipe 13, a vertical driving part 60 for vertically moving the aspiration pipe 13, a aspiration mechanism for releasing the inside of said blood collecting tube 3 to atmospheric air and aspirating the sample in the blood collecting tube 3, and a controller for controlling the operations of the horizontal driving part, vertical driving part and aspiration mechanism. The sample preparation part according to the embodiment is also provided with a vertical sliding part 40 horizontally moved by the horizontal driving part 20. The vertical sliding part 40 holds the blood collecting tube 3, and can be vertically moved by the guide mechanism.

As long as the aspiration pipe 13 has a flow channel therein extending in the longitudinal direction and a aspiration port formed near the tip and for aspirating the sample or the air, the aspiration pipe 13 can be used without being particularly limited in the present invention.

Figure 5:
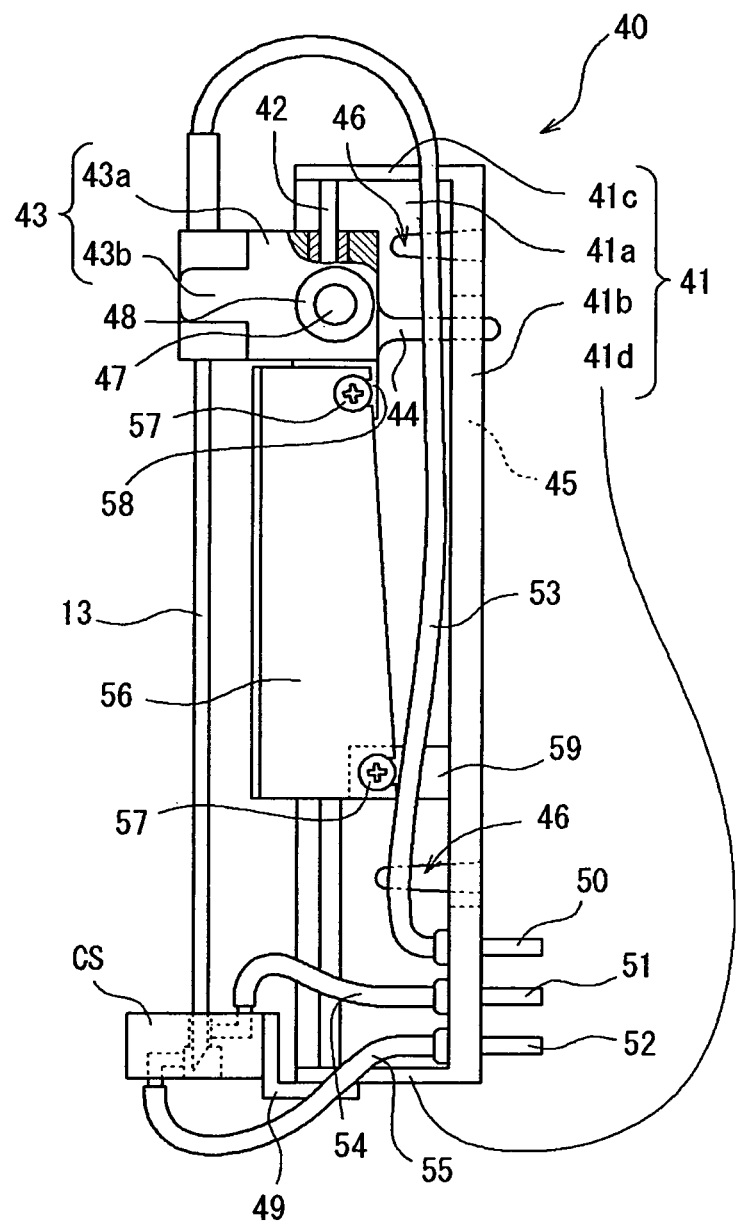
FIG. 5 is a front illustration of a vertical sliding part of the sample analysis apparatus shown in FIG. 1.
Figure 6:
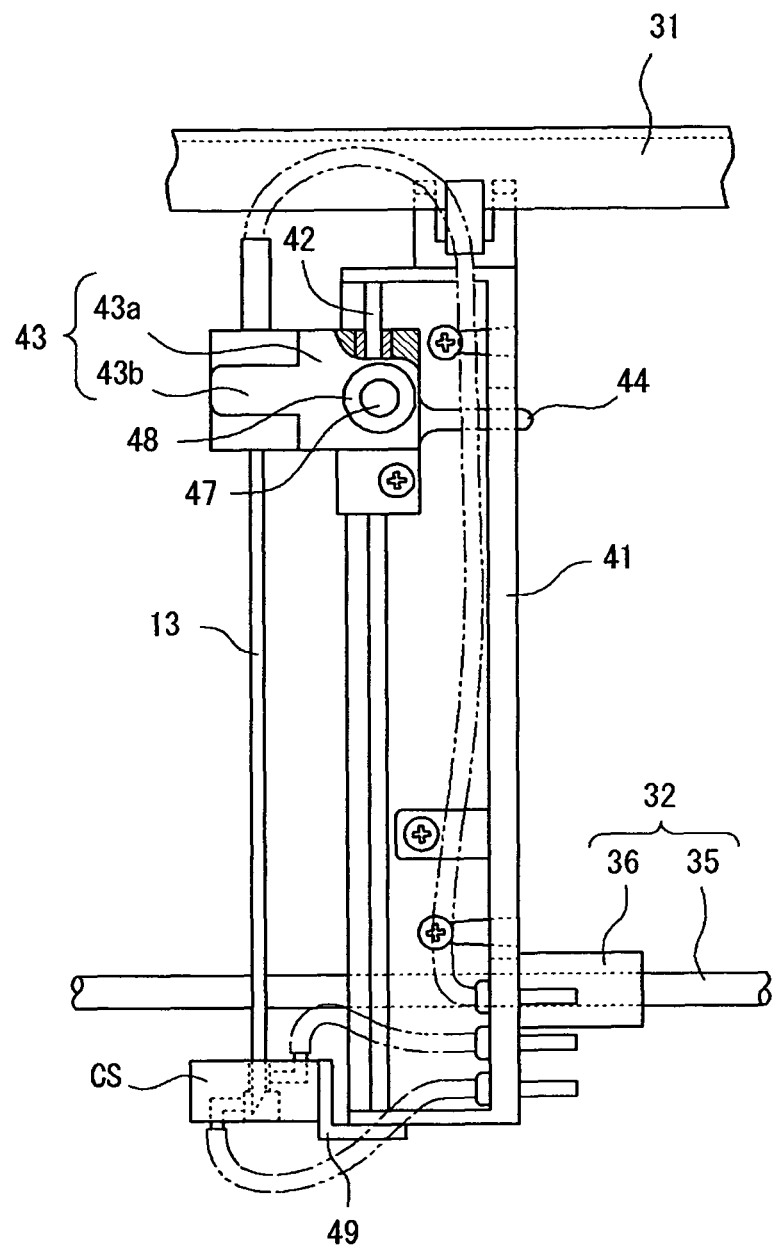
FIG. 6 is a front illustration of the vertical sliding part and horizontal driving part of the sample analysis apparatus shown in FIG. 1.

As shown in the fluid circuit diagrams of FIGS. 5 and 6, a reagent container for accommodating the reagent is provided in the apparatus body 2. Specifically, as the reagent container, there are provided a diluted solution container EPK-V for accommodating a diluted solution (cleaning fluid) EPK, a hemoglobin hemolysis agent container SLS-V for accommodating a hemoglobin hemolysis agent SLS, a hemolysis agent container FFD-V for classifying white blood cells (first reagent container) for accommodating a hemolysis agent FFD for classifying white blood cells, and a staining solution container FFS-V for classifying white blood cells (second reagent container) for accommodating a staining solution FFS for classifying white blood cells.

Figure 4:
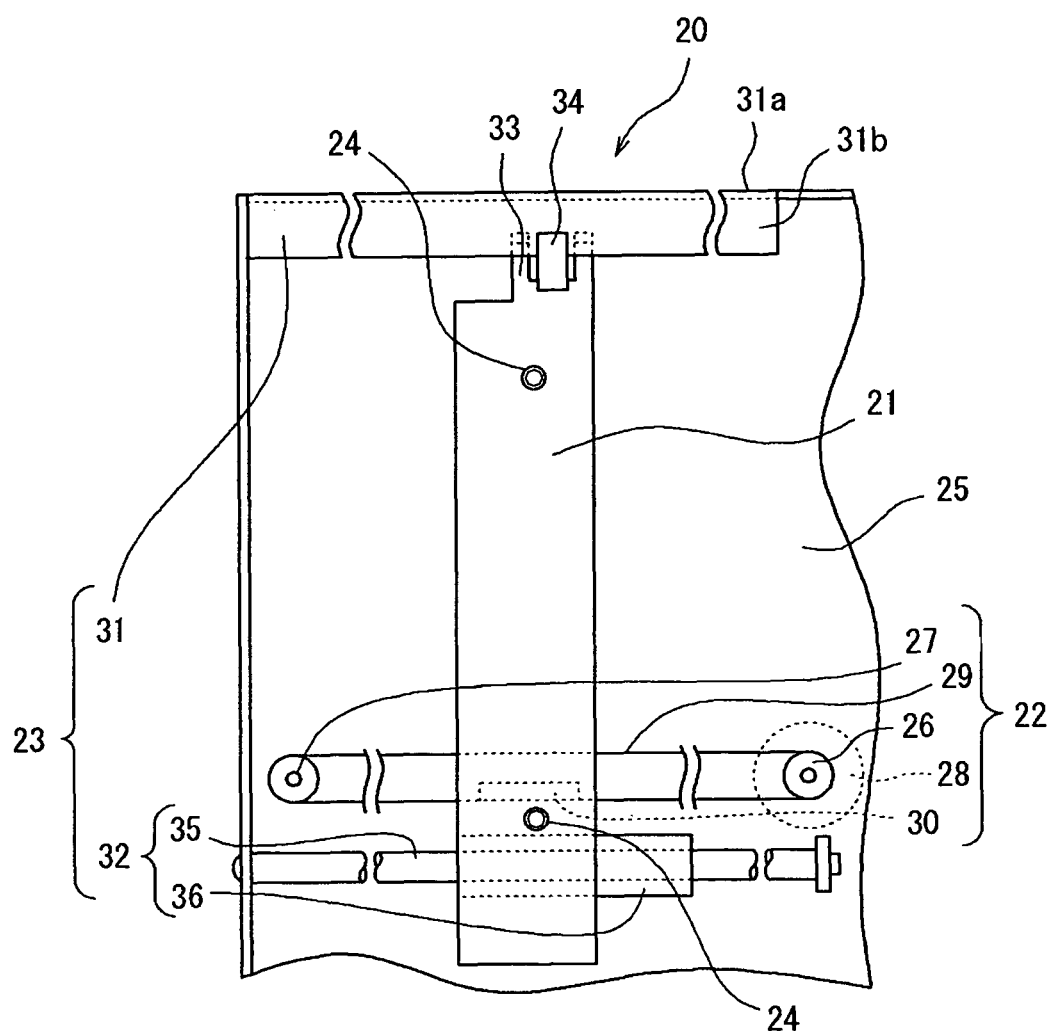
FIG. 4 is a front illustration of a horizontal driving part of the sample analysis apparatus shown in FIG. 1.

FIG. 4 is a front illustration of a horizontal driving part of the sample analysis apparatus shown in FIG. 1. As shown in FIG. 4, the horizontal driving part 20 is provided with a move panel 21 to which a vertical sliding part 40 (the details will be described later) is fixed, a drive mechanism 22 for horizontally moving the move panel 21, and a guide mechanism 23 for guiding the horizontal movement of the move panel 21. The move panel 21 is composed of a long longitudinal plate made of metal or a synthetic resin, and a screw hole 24 for fixing the vertical sliding part 40 is formed in the upper part and lower part thereof. The drive mechanism 22 is composed of a driving pulley 26 and driven pulley 27 rotatably provided on the surface (the surface of the near side in FIG. 4) of a support panel 25, a stepping motor 28 arranged at the back surface side of the support panel 25 and rotating and driving the driving pulley 26, a timing belt 29 stretched between the driving pulley 26 and the driven pulley 27, and a connecting member 30 fixed to both the inner circumferential surface of the timing belt 29 and the back surface of the move panel 21.

An upper guide 31 for guiding the upper end of the move panel 21 is arranged at the upper edge of the support panel 25. On the other hand, a lower guide 32 for guiding the lower part of the move panel 21 is provided below the timing belt 29 on the surface of the support panel 25. The guide mechanism 23 is composed of the upper guide 31 and the lower guide 32.

The upper guide 31 is composed of a horizontal part 31a projected to the surface side from the upper edge of the support panel 25, and a vertical part 31b hung downward from the tip of the horizontal part 31a. The vertical part 31b is held by a back surface side holding piece 33 formed near the upper end of the move panel 21 and a surface side holding piece 34 projected to the surface side near the upper end and having an approximately C shape in section. On the other hand, the lower guide 32 is provided with a guide shaft 35 arranged in parallel to the move direction of the timing belt 29 below the timing belt 29, and a sliding member 36 having a passage in which the guide shaft 35 can be slid. The sliding member 36 is fixed to the back surface of the move panel 21.

When the stepping motor 28 is driven in the configuration, the connecting member 30 fixed to the timing belt 29 is moved in the left or right direction in FIG. 3, and thereby the move panel 21 fixed to the connecting member 30 can be moved in the left or right direction. Since the upper end and lower part vicinities of the move panel 21 are respectively guided by the upper guide 31 and the lower guide 32 in this case, the move panel 21 can be smoothly moved without jolting in all the horizontal directions or in the vertical direction when moving.

Figure 7:
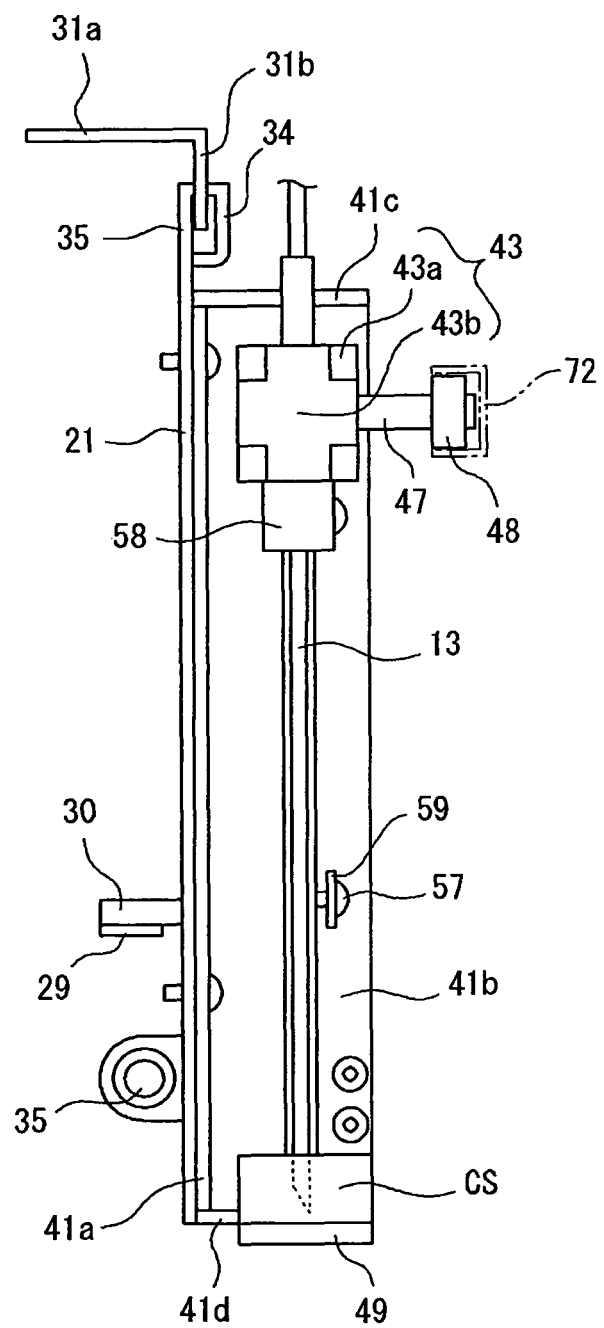
FIG. 7 is a left side illustration of the vertical sliding part and horizontal driving part of the sample analysis apparatus shown in FIG. 1.

Next, the vertical sliding part 40 will be explained in detail. FIG. 5 is a front illustration of a vertical sliding part of the sample analysis apparatus S shown in FIG. 1. FIG. 6 is a front illustration of the vertical sliding part and horizontal driving part. FIG. 7 is a left side illustration of the vertical sliding part and horizontal driving part. As shown in FIGS. 5 to 7, the vertical sliding part 40 has a support 41, a guide shaft 42 vertically supported by the support 41, and a aspiration pipe holding part 43 for holding the aspiration pipe 13 and sliding on the guide shaft 42.

The support 41 is composed of a long longitudinal back surface part 41a in parallel to the move panel 21 or the support panel 25, a long longitudinal side surface part 41b vertically provided to the back surface part 41a, and an upper surface part 41c and lower surface part 41d provided vertically to the back surface part 41a at the upper and lower ends of the back surface part 41a. A long longitudinal guide slit 45 for guiding a guide bar 44 horizontally projected from the aspiration pipe holding part 43 is formed in the side surface part 41b. The guide shaft 42 is vertically supported between the upper surface part 41c and the lower surface part 41d. Numeral 46 designates a notch part formed in the back surface part 41a so as to make a screw which fixes the vertical sliding part 40 to the move panel 21 of the horizontal driving part 20 penetrate.

The aspiration pipe holding part 43 is provided with a sliding part 43a composed of an approximately cube, and an engaging part 43b formed in one surface (the surface of the left side in FIG. 5) of the sliding part 43a. As shown in FIG. 7, the engaging part 43b has a section of a cross shape, and is engaged with a recessed part having a section of a cross shape of an arm of a vertical driving part to be described later to move the aspiration pipe 13 vertically. An shaft 47 is projected on the other surface (the surface of the near side on the plane of the drawing in FIG. 5) of the sliding part 43a, and a guide roller 48 is rotatably attached to the shaft 47. The guide roller 48 is engaged with a guide arm of a vertical driving part 60 to be described later, the aspiration pipe holding part 43 interlocks with the guide arm to be vertically moved.

A cleaning device CS for cleaning the inner and outer circumferences of the aspiration pipe 13 is fixed to the lower surface part 41d of the support 41 via a bracket 49. Nipples 50, 51, 52 for supplying and discharging liquid are fixed to the lower part of the side surface part 41b of the support 41, and are respectively connected to the base end of the aspiration pipe 13 via tubes 53, 54, 55 and the cleaning device CS.

Numeral 56 designates a platy spacer, and is fixed to a fixing part 58 provided on the lower surface of the sliding part 43a and a projection part 59 projected on side surface part 41b of the support 41 by a screw 57. The spacer 56 fixes the aspiration pipe holding part 43 to the top part of the support 41, and prevents the sharp tip of the aspiration pipe 13 from coming out of the cleaning device CS.

That is, when the vertical sliding part 40 is loaded on the horizontal driving part 20, the vertical sliding part 40 is abutted on the move panel 21 of the horizontal driving part 20 in a state where the spacer 56 is attached. After the vertical sliding part 40 is fixed to the screw hole 24 via the notch part 46, the spacer 56 is removed by loosening the screw 57. Thereby, a worker is not injured by the tip of the aspiration pipe, and the vertical sliding part 40 can be safely loaded on the horizontal driving part 20. When problems such as clog in the aspiration pipe 13 are generated, the overall vertical sliding part 40 containing the aspiration pipe 13 is exchanged. However, even in such a case, the exchanging work can be safely performed by using the spacer 56. Though the spacer 56 is usually attached at the time of the factory shipment and exchange of the overall vertical sliding part 40, the spacer 56 is removed at the time of the other operation or the like of the device (see FIG. 6).

Figure 8:
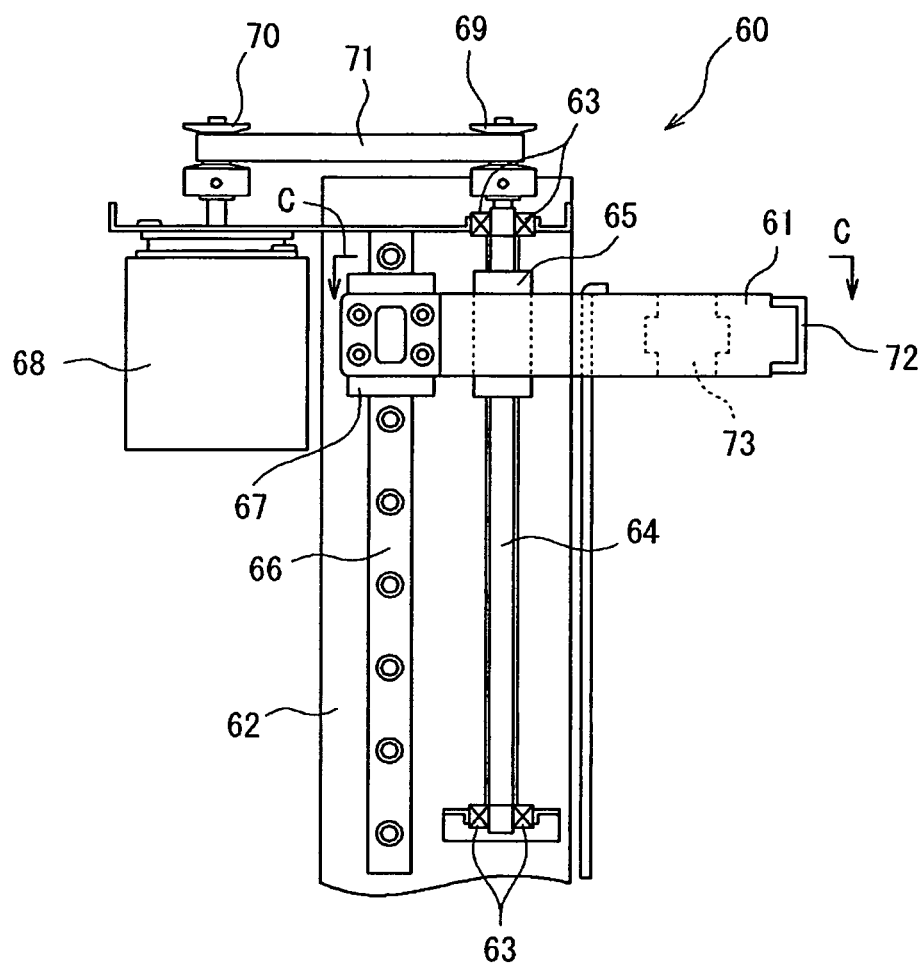
FIG. 8 is a left side illustration of the vertical driving part of the sample analysis apparatus shown in FIG. 1.
Figure 9:
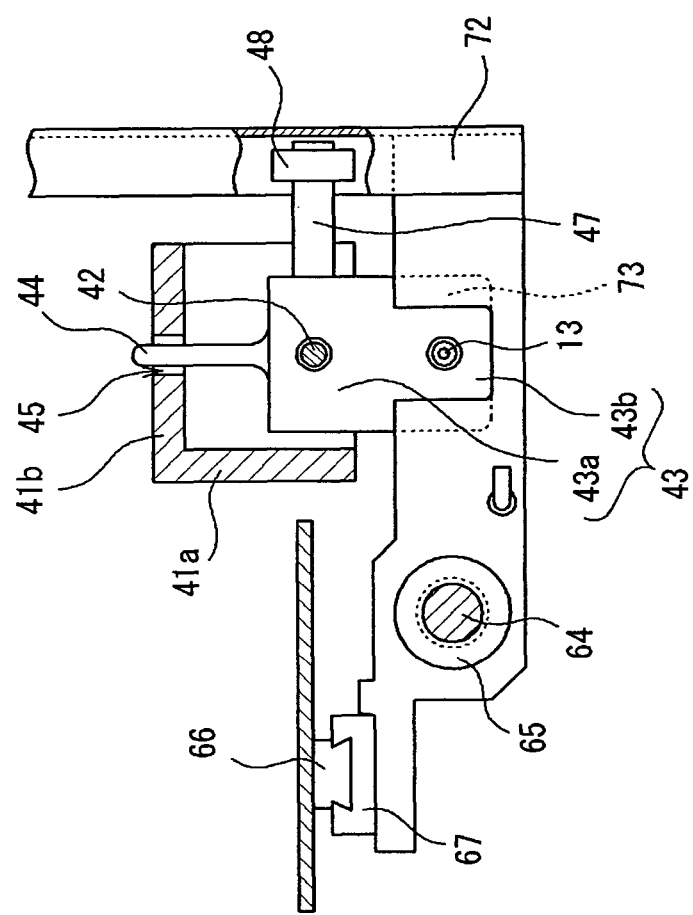
FIG. 9 is a sectional view of FIG. 8 taken along line C-C.
Figure 10:
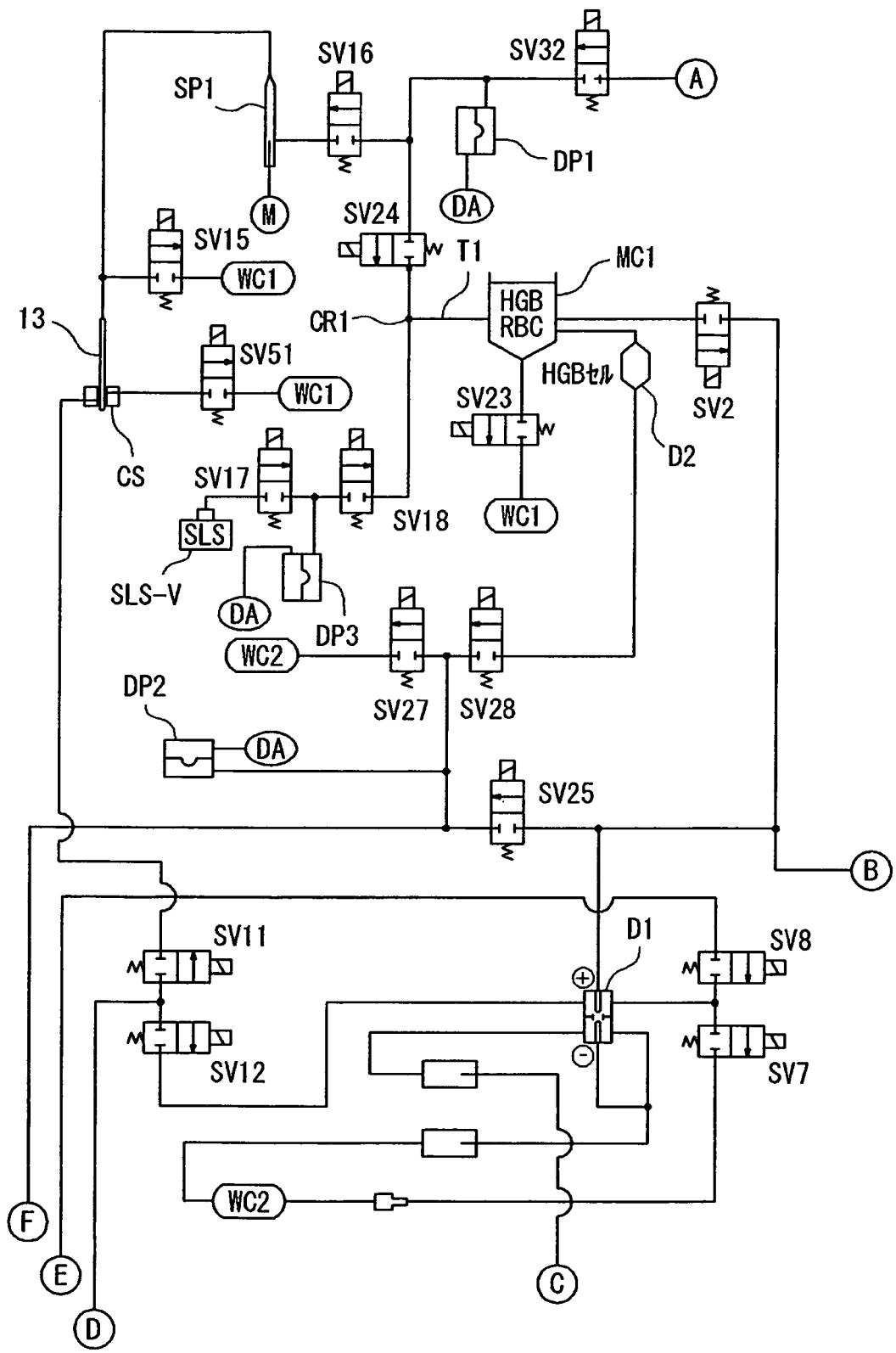
FIG. 10 is a front half part of a fluid circuit diagram of the sample analysis apparatus shown in FIG. 1.
Figure 11:
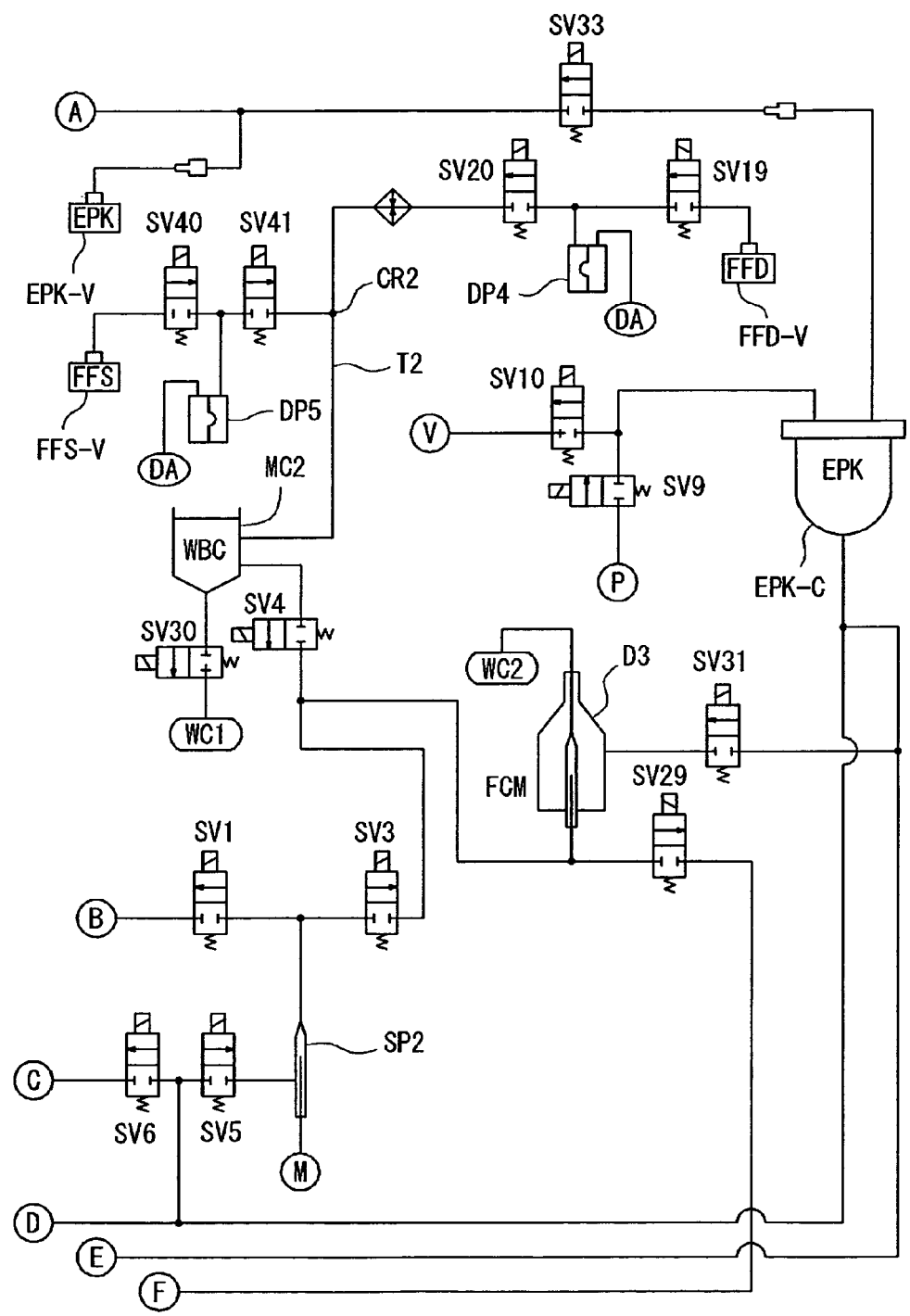
FIG. 11 is a rear half part of the fluid circuit diagram of the sample analysis apparatus shown in FIG. 1.
Figure 12:
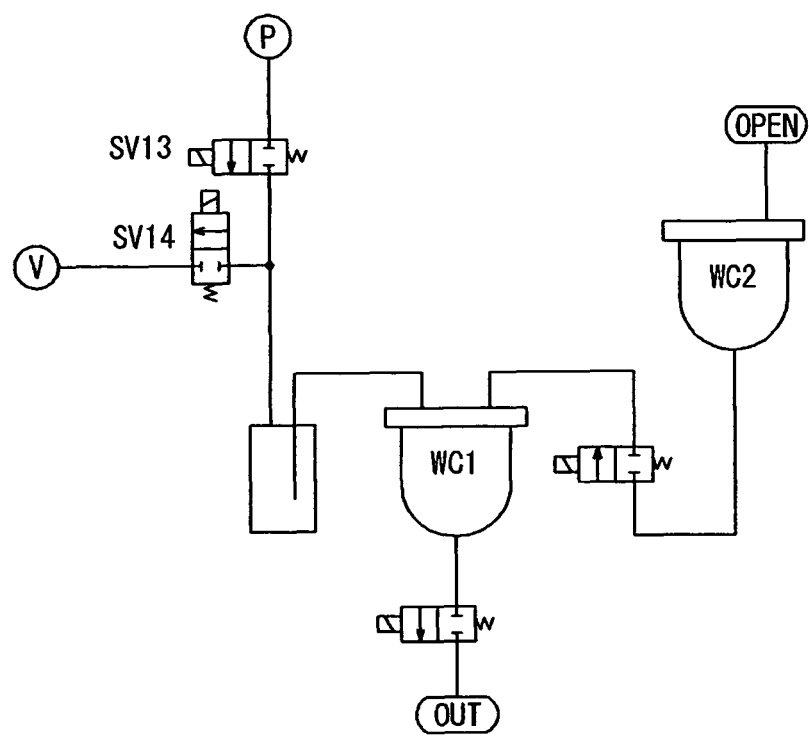
FIG. 12 is a fluid circuit diagram around a drain chamber.
Figure 13:
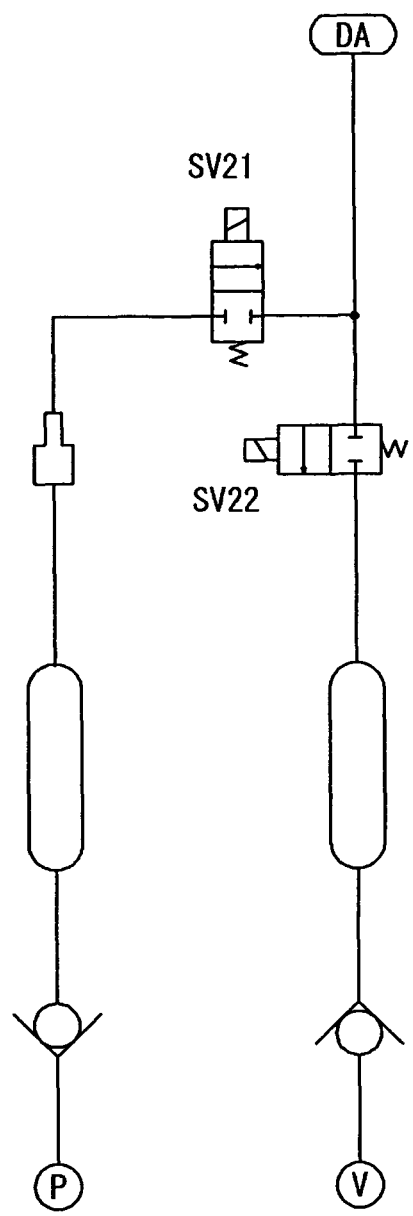
FIG. 13 is a fluid circuit diagram around a diaphragm pump.

Next, the vertical driving part 60 of the aspiration pipe 13 will be explained in detail. FIG. 8 is a left side illustration of the vertical driving part of the sample analysis apparatus S shown in FIG. 1. FIG. 9 is a sectional view of FIG. 8 taken along line C-C. The aspiration pipe moving mechanism of the liquid sample aspiration device according to the present invention is composed of the vertical driving part 60 and the vertical sliding part 40 described above. As shown in FIG. 8, the vertical driving part 60 has an arm 61 composed of a slender body arranged along the horizontal direction, a screw shaft 64 supported rotatably by a bearing 63 penetrating the arm 61 in the orthogonal direction (vertical direction) and arranged on the support panel 62, a nut part 65 having a thread part screwed with the screw shaft 64 and fixed to the arm 61, a slide rail 66 arranged on the support panel 62 so as to be parallel to the screw shaft 64, a sliding member 67 provided at the end part (inner side edge part of the apparatus body 2) of the arm 61 and slidably engaged with the slide rail 66 and vertically guiding the arm 61, and a stepping motor 68 fixed to the support panel 62.

Pulleys 69, 70 are respectively fixed to the upper end of the screw shaft 64 and the output shaft of the stepping motor 68, and a timing belt 71 is stretched between the pulleys 69, 70. A guide arm 72 (see FIG. 8) of a U-shaped section, engaged with the guide roller 48 of the vertical sliding part 40 is horizontally (vertical to the plane of the drawing in FIG. 8) fixed to the other end (the edge part of the surface side of the apparatus body 2) of the arm 61.

The arm 61 has a recessed part 73 having a section of a cross shape, formed on a surface facing the engaging part 43b having a section of a cross shape of the aspiration pipe holding part 43 near the end part of the side of the guide arm 72. As shown in FIG. 9, the engaging part 43b is inserted into the recessed part 73 having the section of the cross shape while maintaining moderate clearance from an arrow X direction. The aspiration pipe 13 is positioned so that the aspiration pipe 13 is positioned immediately above the blood collecting tube 3 in the inserted state. When the aspiration pipe 13 punctures the cap 3a of the blood collecting tube 3, the force of the vertical motion of the arm 61 is directly transmitted to the aspiration pipe holding part 43.

The drives of the stepping motor 28 of the horizontal driving part 20 explained above and stepping motor 68 of the vertical driving part 60 are suitably controlled by the controller of the apparatus body 2. Thereby, the sample can be sucked from the blood collecting tube 3 and the sample can be supplied to a mixed chamber to be described later by horizontally or vertically driving the aspiration pipe holding part 43, that is, the aspiration pipe 13. Since the operation in which the aspiration pipe 13 punctures the cap 3a of the blood collecting tube 3 is included at the time of aspirating the sample, the engaging part 43b of the aspiration pipe holding part 43 is fitted into the recessed part 73 having the section of the cross shape of the arm 61, and large force is transmitted to the aspiration pipe holding part 43. On the other hand, when the aspiration pipe 13 is moved onto the mixed chamber, and the sample is supplied to the mixed chamber, the driving force of the stepping motor 68 of the vertical driving part 60 is transmitted to the aspiration pipe holding part 43 via the arm 61, the guide arm 72 and the guide roller 48.

As shown in FIGS. 2 and 3, the sample analysis apparatus S according to the embodiment is provided with a first mixing chamber MC1 for preparing the mixed sample for performing the measurement relating to red blood cells, hemoglobin and blood platelets, a second mixing chamber MC2 for preparing the mixed sample for performing the measurement relating to white blood cells, a first detector D1 for performing the measurement relating to red blood cells, a second detector D2 for performing the measurement relating to hemoglobin, and a third detector D3 for performing the measurement relating to white blood cells.

As shown in FIG. 14, the apparatus body 2 is provided with a controller 100 for controlling the sample preparation part and the measuring parts D1, D2, D3. The apparatus body 2 is also provided with a driving circuit 110 for driving electromagnetic valves SV1 to SV33, SV40, SV41 in a fluid circuit constituting the sample preparation part or the like and the various pump motors 28, 68, SP1, SP2, P, V, DP1, DP2, DP3, DP4, DP5 or the like. The controller 100 drives the electromagnetic valves or the like via a driving circuit 110. The controller 100 can be communicated with the processing unit PC via a communication interface which is not shown, and various signals and data or the like can be communicated between the controller 100 and the processing unit PC.

Next, a method for aspirating a liquid sample according to the embodiment of the present invention will be explained referring to a fluid circuit diagram shown in FIGS. 10 to 13 and a flow chart shown in FIG. 15. In FIGS. 10 to 13, numerals SP1, SP2 designate syringe pumps for aspirating and supplying the sample (blood), and numeral CS designates a cleaning spit for cleaning the aspiration pipe. Numerals DP1 to DP5 designate diaphragm pumps for determining the quantity of fluids such as a diluted solution, a hemolysis agent and a staining solution. Numerals WC1 to WC2 designate drain chambers. Numerals EPK-C designates an EPK (diluted solution) accommodating container. Numerals SV1 to SV33 designate magnetic valves for opening and closing a flow channel. These valves SV1 to SV33 are those of a normally closed type that are usually closed.

The method for aspirating the liquid sample according to the embodiment comprises: a first insertion step of piercing the cap by using the aspiration pipe 13 to insert the aspiration pipe 13 into the blood collecting tube 3, and make the inside of the blood collecting tube 3 communicate with atmosphere; a fluid filling step of drawing out the aspiration pipe 13 from the blood collecting tube 3 and filling the aspiration pipe 13 with the diluted solution; and a second insertion step of piercing the cap by using the aspiration pipe 13 again and inserting the aspiration pipe 13 into the blood collecting tube 3 to suck the blood in the blood collecting tube 3. Hereinafter, the method for aspirating the liquid sample will be explained in sequence.

(1) When the power supply of the apparatus is turned on, and a predetermined preparative step such as the transportation of the diluted solution to the diluted solution accommodating container EPK-C is completed, standby is displayed. The blood collecting tube 3 is set in the apparatus body 2 in this state, and the mode is selected. A start button is then pushed, and the aspiration step of the sample is started.

(2) First, a valve SV14 is opened, and change the inside of the drain chamber WC1 is set to a negative pressure state. The valve SV14 is opened at the time of the previous measurement end at the time of continuous measurement, and the inside of the drain chamber WC1 is set to the negative pressure state. A valve SV15 is then opened, the diluted solution (EPK) in the aspiration pipe 13 is sucked, and the inside of the aspiration pipe 13 is set to an empty state. Next, the valve SV15 is closed, and a valve SV23 is opened to empty the first mixing chamber MC1 and the discharge line thereof (Step S1).

(3) A valve SV14 is then closed, and the drain chamber WC1 is released to atmospheric air. The valve SV15 is then opened, and a line leading to the first mixing chamber MC1 through the drain chamber WC1 from the aspiration port of the aspiration pipe and containing the first flow channel is released to atmospheric air (Step S2).

(4) Though the aspiration pipe 13 is located at a first position of the outside of the blood collecting tube 3 in the steps S1 and S2, the aspiration pipe 13 punctures the cap 3a of the blood collecting tube 3 after the step S2 is ended, and the aspiration pipe 13 is dropped to a second position where the aspiration port of the tip thereof is located above the sample. Thereby, the inside of the blood collecting tube 3 is released to atmospheric air through a line leading to the first mixing chamber MC1 through the drain chamber WC1 from the aspiration port of the aspiration pipe (Step S3).

(5) The valve SV15 and the valve SV23 are then closed, and the valve SV14 is opened to set the first drain chamber WC1 to a negative pressure state.

(6) The aspiration pipe 13 is then raised from the second position. The tip of the aspiration pipe 13 is escaped from cap 3a of the blood collecting tube 3, and at the same time, the valve SV11 and the valve SV51 are opened. The outer circumference of the aspiration pipe 13 is cleaned with the rise operation of the aspiration pipe 13 (Step S4).

(7) The valve SV21, the valve SV15 and the valve SV16 are opened, and the valve SV15 is closed after 0.2 seconds. Thereby, a positive pressure is applied to a diaphragm pump DP1 of 1.0 mL for diluted solution as the first pump, and the insides of the sample aspiration line containing the second flow channel and aspiration pipe 13 are filled with the diluted solution (Step S5). The excessive diluted solution coming out of the aspiration port of the aspiration pipe 13 is sucked from the cleaning device CS.

(8) The valve SV11 and the valve SV51 are closed, and the cleaning of the aspiration pipe 13 is ended.

(9) After the rising operation of the aspiration pipe 13 is completed, the aspiration pipe 13 is dropped by about several mm again, and the aspiration port of the tip of the aspiration pipe 13 is emitted from the cleaning device CS. The diluted solution of 3 μL is then sucked by the syringe pump SP1, and an air gap is formed at the tip of the aspiration pipe 13 (Step S6).

(10) The aspiration pipe 13 is dropped to the third position, and the aspiration port is put into the sample. The sample of a predetermined amount is sucked in this state by the syringe pump SP1 as the second pump (Step S7).

The aspiration step of the sample is completed by the above steps S1 to S7, and the mixed sample for analysis is prepared in the first mixing chamber MC1 or second mixing chamber MC2 by using the sample sucked into the aspiration pipe 13. The number of red blood cells, hemoglobin, the number of white blood cells or the like are measured by using the mixed sample for analysis by the first detector D1, the second detector D2 or the third detector D3.

Specifically, after aspirating the sample at Step S7, the aspiration pipe 13 is raised. The tip of the aspiration pipe 13 is escaped from the cap 3a of the blood collecting tube 3, and at the same time, the valve SV11 and the valve SV51 are opened. The outer circumference of the aspiration pipe 13 is cleaned with the rising operation of the aspiration pipe 13.

The move panel 21 holding the aspiration pipe 13 and the cleaning device CS is horizontally moved by the horizontal driving part 20 after the cleaning of the aspiration pipe 13 is ended, and is stopped above the first mixing chamber MC1. The sample of a predetermined amount is discharged to the first mixing chamber MC1 from the aspiration pipe 13.

Next, the move panel 21 holding the aspiration pipe 13 and the cleaning device CS is horizontally moved by the horizontal driving part 20, and is stopped above the second mixing chamber MC2. The sample of a predetermined amount is discharged to the second mixing chamber MC2 from the aspiration pipe 13.

After the discharge is ended, the aspiration pipe 13 is raised, and the outer circumference of the aspiration pipe 13 is cleaned by the cleaning device CS. The rise of the aspiration pipe 13 is stopped when the tip of the aspiration pipe 13 comes in the cleaning device CS. The diluted solution is supplied to the aspiration pipe 13 from the tube 53, and the inner side of the aspiration pipe 13 is cleaned. The diluted solution discharged from the aspiration port of the aspiration pipe 13 is discharged via a tube 54.

Though the outer circumference of the aspiration pipe is cleaned at Step S4 in the above embodiment, it is not necessary to always clean the outer circumference of the aspiration pipe, and such cleaning step may be omitted.

What is claimed is:

1. A method for measuring a blood sample in a container sealed by a cap, comprising the steps of:

performing a first piercing of the cap of the container by inserting a tip of an aspiration pipe, which comprises a flow channel extending in a longitudinal direction and an aspiration opening connecting to the flow channel and formed near the tip, into the sealed container to communicate an interior of the sealed container with atmosphere through the flow channel;

drawing out the aspiration pipe from the sealed container communicated with the atmosphere;

supplying a diluted solution from a base end side of the aspiration pipe to fill the flow channel of the drawn out aspiration pipe with the diluted solution;

forming an air gap in an aspiration opening side of the filled flow channel by aspirating from the base end side of the aspiration pipe;

performing a second piercing of the cap by inserting the air gap-formed and diluted solution-filled aspiration pipe into the sealed container;

aspirating the blood sample in the sealed container from the aspiration opening of the air gap-formed and diluted solution-filled aspiration pipe;

drawing out the blood sample-aspirated aspiration pipe from the sealed container;

transporting the blood sample-aspirated aspiration pipe to a measurement sample preparing container;

discharging the aspirated blood sample into the measurement sample preparing container from the aspiration opening of the aspiration pipe; and measuring a measurement sample prepared in the measurement sample preparing container, wherein the method is an automated method.

2. The method of claim 1, further comprising cleaning an exterior of the aspiration pipe using the diluted solution while pulling out the aspiration pipe from the cap between the aspirating and the discharging.

3. The method of claim 1, further comprising: cleaning an exterior of the aspiration pipe using the diluted solution; and supplying the diluted solution from the base end side of the aspiration pipe to clean an inner side of the aspiration pipe using the diluted solution after the discharging.

4. The method of claim 1, wherein the discharging comprises discharging a part of the aspirated blood sample into the measurement sample preparing container; and wherein the method further comprises: discharging the blood sample into a second measurement sample preparing container; and measuring a second measurement sample prepared in the second measurement sample preparing container after the discharging.

5. The method of claim 4, further comprising cleaning an exterior of the aspiration pipe using the diluted solution; and supplying the diluted solution from the base end side of the aspiration pipe to clean an inner side of the aspiration pipe using the diluted solution after the discharging of the blood sample into the second measurement sample preparing container.

6. The method of claim 1, wherein the measuring comprises a measurement selected from the group consisting of measurement of number of red blood cells, measurement of number of white blood cells, measurement of hemoglobin, classification of the white blood cells, and combinations thereof.

7. An apparatus for measuring a blood sample in a container sealed by a cap, comprising:

an aspiration pipe for piercing the cap of the container and aspirating the blood sample in the sealed container, wherein the aspiration pipe comprises a first flow channel extending in a longitudinal direction and an aspiration opening formed near the tip;

an aspiration pipe moving mechanism for moving the aspiration pipe to an outside position of the sealed container, a first position where the aspiration opening is located above the blood sample in the container, and a second position where the aspiration opening is located in the blood sample in the container;

a fluid mechanism comprising a second flow channel released to atmospheric air, a diluted solution accommodating part for accommodating a diluted solution, a third flow channel capable of connecting the aspiration pipe to the diluted solution accommodating part, a first pump capable of supplying the diluted solution accommodated in the diluted solution accommodating part to the aspiration pipe via the third flow channel, and a second pump configured for aspirating and discharging the blood sample in the sealed container via the third flow channel, and for selectively communicating the first and the second flow channels with the first flow channel of the aspiration pipe;

a measurement sample preparing container for mixing the blood sample with a reagent to prepare a measurement sample;

a measuring part for measuring an analysis sample prepared in the measurement sample preparing container, wherein the measuring part comprises:

a first detector configured to measure a number of red blood cells in the analysis sample;

a second detector configured to measure hemoglobin in the analysis sample; and a third detector configured to measure a number of white blood cells in the analysis sample; and a controller configured for controlling the aspiration pipe moving mechanism and the fluid mechanism to perform operations comprising:

moving the aspiration pipe such that the aspiration opening is moved to the first position from the outside position;

releasing the inside of the sealed container to atmospheric air via the second flow channel;

moving the aspiration pipe such that the aspiration opening is moved to the outside position from the first position;

supplying the diluted solution into the aspiration pipe via the third flow channel by the first pump to fill the first flow channel with the diluted solution;

forming an air gap in the aspiration opening side of the filled first flow channel by the aspiration of the second pump;

moving the aspiration pipe so that the aspiration opening is moved to the second position from the outside position;

aspirating the blood sample in the sealed container by the second pump;

moving the aspiration pipe such that the aspiration opening is moved to a measurement sample preparing container facing position from the second position; and discharging the aspirated blood sample into the measurement sample preparing container from the aspiration opening of the aspiration pipe.

8. The apparatus of claim 7, further comprising:

a container holder for holding the sealed container so that the cap is located above; and a cleaning device comprising a through-hole for movably accepting the aspiration pipe in the vertical direction, a supply passage for supplying the diluted solution into the through-hole, and a discharge passage for aspirating and discharging the diluted solution supplied in the through-hole;

whereby the cleaning device can clean the aspiration pipe above the sealed container, and the fluid mechanism can supply the diluted solution to the supply passage of the cleaning device and can suck the diluted solution from the discharge passage of the cleaning device.

9. The apparatus of claim 8, further comprising:

a holding member for holding the cleaning device and the aspiration pipe moving mechanism; and a second moving mechanism for moving the holding member.

10. The apparatus of claim 9, wherein the aspiration pipe moving mechanism moves the aspiration pipe vertically, and the second moving mechanism moves the holding member horizontally.

11. The apparatus of claim 9, wherein the second moving mechanism moves the holding member so that the position of the aspiration pipe is moved to the upper part of the measurement sample preparing container from the upper part of the sealed container after the aspiration pipe aspirates the blood sample.

12. The method of claim 1, wherein the first piercing is performed by inserting the aspiration pipe to a first position where the aspiration opening is located above the blood sample in the container.

13. The method of claim 12, wherein the second piercing is performed by inserting the aspiration pipe to a second position where the aspiration opening is located in the blood sample in the container.

\* \* \* \* \*